United States Patent
Augoyard et al.

(10) Patent No.: US 10,022,167 B2
(45) Date of Patent: Jul. 17, 2018

(54) METHOD OF OSTEOSYNTHESES OR ARTHRODESIS OF TWO-BONE PARTS, IN PARTICULAR OF THE HAND AND / OR FOOT

(71) Applicant: Stryker European Holdings I, LLC, Kalamazoo, MI (US)

(72) Inventors: Marc Augoyard, Tassin la Demi Lune (FR); Jacques Peyrot, Tassin la Demi Lune (FR); Tristan Meusnier, Saint-Etienne (FR); Bernard Prandi, Rennes (FR)

(73) Assignee: Stryker European Holdings I, LLC, Kalamazoo, MI (US)

( * ) Notice: Subject to any disclaimer, the term of this patent is extended or adjusted under 35 U.S.C. 154(b) by 0 days.

(21) Appl. No.: 15/292,955

(22) Filed: Oct. 13, 2016

(65) Prior Publication Data

US 2017/0027626 A1    Feb. 2, 2017

Related U.S. Application Data

(63) Continuation of application No. 13/896,894, filed on May 17, 2013, now Pat. No. 9,492,215, which is a
(Continued)

(30) Foreign Application Priority Data

Apr. 14, 2005    (FR) ..................................... 05 50957

(51) Int. Cl.
*A61B 17/84*    (2006.01)
*A61B 17/72*    (2006.01)
(Continued)

(52) U.S. Cl.
CPC .......... *A61B 17/7291* (2013.01); *A61B 17/68* (2013.01); *A61B 17/72* (2013.01);
(Continued)

(58) Field of Classification Search
CPC ............ A61B 17/7067; A61B 17/7291; A61B 17/0642
See application file for complete search history.

(56) References Cited

U.S. PATENT DOCUMENTS

| 1,095,054 A | | 4/1914 | Wiesenfeld |
| 1,517,334 A | * | 12/1924 | Young ...................... A45D 8/12 132/158 |

(Continued)

FOREIGN PATENT DOCUMENTS

| CA | 2551021 A1 | 3/2005 |
| CA | 2243699 C | 1/2006 |

(Continued)

OTHER PUBLICATIONS

International Search Report, PCT/FR2006/050345, dated Aug. 30, 2006.
(Continued)

*Primary Examiner* — Christian Sevilla
(74) *Attorney, Agent, or Firm* — Lerner, David, Littenberg, Krumholz & Mentlik, LLP

(57) ABSTRACT

In one embodiment, the present invention is a fixation device including a median zone having a substantially triangular shape; a first fixation zone including first and second tabs that, in a separated configuration, extend away from each other from an end of the median zone, the first fixation zone having a first region adjacent the median zone and a second region adjacent the first region. Also, within the first region of the first fixation zone, an inner surface of each of the first and second tabs of the first fixation zone extends outwardly and proximally from the median zone to a first point to form an arch, and from the first point, the inner surface of each of the first and second tabs extends toward a second point. Further, within the second region of the first fixation zone, the inner surface of each of the first and second tabs of the
(Continued)

first fixation zone extends outwardly from each second point to a respective third point so that the inner surface of each of the first and second tabs from the second point to the third point is arcuate and convex.

20 Claims, 2 Drawing Sheets

Related U.S. Application Data continuation of application No. 11/911,405, filed as application No. PCT/FR2006/050345 on Apr. 12, 2006, now Pat. No. 8,475,456.

(51) Int. Cl.
  *A61B 17/68* (2006.01)
  *A61B 17/00* (2006.01)
  *A61F 2/30* (2006.01)
  *A61F 2/42* (2006.01)

(52) U.S. Cl.
  CPC ...... *A61B 17/7208* (2013.01); *A61B 17/7225* (2013.01); *A61B 17/7258* (2013.01); *A61B 17/7266* (2013.01); *A61B 17/844* (2013.01); A61B 2017/00867 (2013.01); A61B 2017/681 (2013.01); A61F 2002/30093 (2013.01); A61F 2002/30622 (2013.01); A61F 2002/4243 (2013.01); A61F 2210/0019 (2013.01)

(56) References Cited

U.S. PATENT DOCUMENTS

| | | | |
|---|---|---|---|
| 1,893,864 A * | 1/1933 | Kocher | A45D 24/02 132/157 |
| 2,580,821 A * | 1/1952 | Nicola | A61B 17/8004 322/2 A |
| 2,984,248 A * | 5/1961 | Sidelman | A45D 8/12 132/158 |
| 3,462,765 A | 8/1969 | Swanson | |
| 3,466,669 A * | 9/1969 | Flatt | A61F 2/4241 623/21.17 |
| 3,593,342 A | 7/1971 | Niebauer et al. | |
| 3,681,786 A | 8/1972 | Lynch | |
| 3,739,403 A | 6/1973 | Nicolle | |
| 3,805,302 A | 4/1974 | Mathys | |
| 3,824,631 A * | 7/1974 | Burstein | A61B 17/68 623/23.39 |
| 3,875,594 A | 4/1975 | Swanson | |
| D243,716 S | 3/1977 | Treace et al. | |
| 4,091,806 A | 5/1978 | Aginsky et al. | |
| 4,158,893 A | 6/1979 | Swanson | |
| 4,204,284 A | 5/1980 | Koeneman | |
| 4,276,660 A | 7/1981 | Laure | |
| 4,364,382 A | 12/1982 | Mennen | |
| 4,367,562 A | 1/1983 | Gauthier et al. | |
| 4,485,816 A * | 12/1984 | Krumme | A61B 17/0644 219/201 |
| D277,509 S | 2/1985 | Lawrence et al. | |
| D277,784 S | 2/1985 | Sgarlato et al. | |
| 4,522,200 A | 6/1985 | Stednitz | |
| D284,099 S | 6/1986 | Laporta et al. | |
| 4,634,382 A | 1/1987 | Kusano et al. | |
| D291,731 S | 9/1987 | Aikins | |
| 4,759,768 A | 7/1988 | Hermann et al. | |
| 4,871,367 A | 10/1989 | Christensen et al. | |
| 4,905,679 A * | 3/1990 | Morgan | A61B 17/8085 227/156 |
| 4,955,916 A | 9/1990 | Carignan et al. | |
| 4,969,909 A * | 11/1990 | Barouk | A61B 17/72 606/62 |
| 5,011,497 A | 4/1991 | Persson et al. | |
| 5,047,059 A | 9/1991 | Saffar | |
| 5,062,851 A | 11/1991 | Branemark | |
| 5,074,865 A * | 12/1991 | Fahmy | A61B 17/6425 606/105 |
| 5,092,896 A | 3/1992 | Meuli et al. | |
| 5,108,443 A | 4/1992 | Branemark | |
| 5,133,761 A | 7/1992 | Krouskop | |
| 5,179,915 A * | 1/1993 | Cohen | A61B 17/1717 606/62 |
| 5,190,546 A | 3/1993 | Jervis | |
| 5,207,712 A * | 5/1993 | Cohen | A61B 17/68 606/300 |
| 5,326,364 A | 7/1994 | Clift, Jr. et al. | |
| 5,360,450 A | 11/1994 | Giannini | |
| 5,405,400 A | 4/1995 | Linscheid et al. | |
| 5,405,401 A | 4/1995 | Lippincott, III et al. | |
| 5,425,776 A | 6/1995 | Cohen | |
| 5,425,777 A * | 6/1995 | Sarkisian | A61F 2/30767 606/76 |
| 5,454,814 A | 10/1995 | Comte | |
| 5,464,427 A | 11/1995 | Curtis et al. | |
| 5,474,557 A * | 12/1995 | Mai | A61B 17/0642 606/219 |
| D366,114 S * | 1/1996 | Ohata | D10/61 |
| 5,480,447 A * | 1/1996 | Skiba | A61F 2/4225 623/21.19 |
| 5,484,443 A | 1/1996 | Pascarella et al. | |
| D369,412 S * | 4/1996 | Morgan | D24/140 |
| 5,507,822 A | 4/1996 | Bouchon et al. | |
| 5,522,903 A | 6/1996 | Sokolow et al. | |
| 5,554,157 A | 9/1996 | Errico et al. | |
| 5,578,036 A * | 11/1996 | Stone | A61B 17/688 606/281 |
| 5,634,925 A | 6/1997 | Urbanski | |
| 5,674,297 A | 10/1997 | Lane et al. | |
| 5,690,631 A * | 11/1997 | Duncan | A61B 17/8085 606/281 |
| 5,702,472 A | 12/1997 | Huebner | |
| D388,877 S * | 1/1998 | Morgan | D24/155 |
| 5,725,585 A | 3/1998 | Zobel | |
| 5,779,707 A * | 7/1998 | Bertholet | A61B 17/8004 606/301 |
| 5,782,927 A | 7/1998 | Klawitter et al. | |
| 5,824,095 A | 10/1998 | Di Maio, Jr. et al. | |
| 5,876,434 A * | 3/1999 | Flomenblit | A61C 8/0033 433/172 |
| 5,882,444 A | 3/1999 | Flomenblit et al. | |
| 5,919,193 A | 7/1999 | Slavitt | |
| 5,951,288 A | 9/1999 | Sawa | |
| 5,958,159 A | 9/1999 | Prandi | |
| 5,984,970 A | 11/1999 | Bramlet | |
| 5,984,971 A | 11/1999 | Faccioli et al. | |
| 6,011,497 A | 1/2000 | Tsang et al. | |
| 6,017,366 A | 1/2000 | Berman | |
| 6,093,188 A * | 7/2000 | Murray | A61B 17/8085 606/282 |
| 6,123,709 A * | 9/2000 | Jones | A61B 17/1728 606/280 |
| 6,146,387 A * | 11/2000 | Trott | A61B 17/0469 606/104 |
| 6,162,234 A | 12/2000 | Freedland et al. | |
| 6,193,757 B1 | 2/2001 | Foley et al. | |
| 6,197,037 B1 * | 3/2001 | Hair | A61B 17/688 606/151 |
| 6,200,330 B1 * | 3/2001 | Benderev | A61B 17/0401 411/358 |
| 6,248,109 B1 * | 6/2001 | Stoffella | A61B 17/68 606/327 |
| 6,261,289 B1 | 7/2001 | Levy | |
| 6,319,284 B1 | 11/2001 | Rushdy et al. | |
| 6,325,805 B1 * | 12/2001 | Ogilvie | A61B 17/0642 606/300 |
| 6,342,076 B1 | 1/2002 | Lundborg | |
| 6,348,052 B1 * | 2/2002 | Sammarco | A61B 17/8085 606/284 |
| 6,352,560 B1 | 3/2002 | Poeschmann et al. | |
| 6,383,223 B1 | 5/2002 | Baehler et al. | |
| 6,386,877 B1 | 5/2002 | Sutter | |
| 6,423,097 B2 | 7/2002 | Rauscher | |

(56) References Cited

U.S. PATENT DOCUMENTS

| | | |
|---|---|---|
| 6,428,634 B1 | 8/2002 | Besselink et al. |
| 6,454,808 B1 | 9/2002 | Masada |
| 6,475,242 B1 | 11/2002 | Bramlet |
| 6,554,833 B2 | 4/2003 | Levy et al. |
| 6,689,169 B2 | 2/2004 | Harris |
| 6,692,499 B2* | 2/2004 | Tormala ............... A61B 17/064 411/452 |
| 6,699,247 B2 | 3/2004 | Zucherman et al. |
| 6,699,292 B2 | 3/2004 | Ogilvie et al. |
| 6,706,045 B2 | 3/2004 | Lin et al. |
| 6,773,437 B2 | 8/2004 | Ogilvie et al. |
| 6,811,568 B2 | 11/2004 | Minamikawa |
| 6,827,741 B2 | 12/2004 | Reeder |
| 6,869,449 B2 | 3/2005 | Ball et al. |
| 6,896,177 B2 | 5/2005 | Carter |
| 6,981,974 B2 | 1/2006 | Berger |
| 7,025,789 B2 | 4/2006 | Chow et al. |
| 7,037,342 B2 | 5/2006 | Nilsson et al. |
| 7,041,106 B1* | 5/2006 | Carver ............... A61B 17/7291 606/309 |
| 7,052,498 B2 | 5/2006 | Levy et al. |
| 7,182,787 B2 | 2/2007 | Hassler et al. |
| 7,240,677 B2 | 7/2007 | Fox |
| 7,291,175 B1 | 11/2007 | Gordon |
| 7,588,603 B2 | 9/2009 | Leonard |
| 7,655,042 B2 | 2/2010 | Foley et al. |
| 7,780,737 B2 | 8/2010 | Bonnard et al. |
| 7,837,738 B2 | 11/2010 | Reigstad et al. |
| 7,842,091 B2 | 11/2010 | Johnstone et al. |
| 7,909,880 B1 | 3/2011 | Grant |
| 7,922,765 B2 | 4/2011 | Reiley |
| 7,955,388 B2 | 6/2011 | Jensen et al. |
| 7,976,580 B2 | 7/2011 | Berger |
| 8,048,173 B2 | 11/2011 | Ochoa |
| 8,100,983 B2 | 1/2012 | Schulte |
| 8,162,942 B2 | 4/2012 | Coati et al. |
| 8,202,305 B2 | 6/2012 | Reiley |
| 8,262,712 B2 | 9/2012 | Coilard-Lavirotte et al. |
| 8,308,779 B2 | 11/2012 | Reiley |
| 8,394,097 B2* | 3/2013 | Peyrot ............... A61F 2/30 606/62 |
| 8,414,583 B2* | 4/2013 | Prandi ............... A61B 17/68 606/62 |
| 8,475,456 B2* | 7/2013 | Augoyard ............... A61B 17/68 606/331 |
| 8,529,611 B2 | 9/2013 | Champagne et al. |
| 8,597,337 B2 | 12/2013 | Champagne |
| 8,608,785 B2 | 12/2013 | Reed et al. |
| 8,685,024 B2 | 4/2014 | Roman |
| 8,715,325 B2 | 5/2014 | Weiner et al. |
| 8,840,623 B2 | 9/2014 | Reiley |
| 8,864,804 B2 | 10/2014 | Champagne et al. |
| 9,011,504 B2 | 4/2015 | Reed |
| 9,125,698 B2* | 9/2015 | Miller ............... A61B 17/8085 |
| 9,283,007 B2 | 3/2016 | Augoyard et al. |
| 2001/0025199 A1 | 9/2001 | Rauscher |
| 2001/0049529 A1* | 12/2001 | Cachia ............... A61B 17/68 606/301 |
| 2002/0019636 A1* | 2/2002 | Ogilvie ............... A61B 17/0642 606/75 |
| 2002/0055785 A1 | 5/2002 | Harris |
| 2002/0065561 A1 | 5/2002 | Ogilvie et al. |
| 2002/0068939 A1* | 6/2002 | Levy ............... A61B 17/7258 606/63 |
| 2002/0082705 A1 | 6/2002 | Bouman et al. |
| 2002/0099395 A1* | 7/2002 | Acampora ............... A61B 17/083 606/157 |
| 2002/0133156 A1* | 9/2002 | Cole ............... A61B 17/164 606/62 |
| 2002/0169066 A1 | 11/2002 | Cassidy et al. |
| 2002/0189622 A1* | 12/2002 | Cauthen, III ............... A61F 2/441 128/898 |
| 2003/0040805 A1 | 2/2003 | Minamikawa |
| 2003/0069645 A1* | 4/2003 | Ball ............... A61F 2/4241 623/21.15 |
| 2003/0120277 A1 | 6/2003 | Berger |
| 2003/0130660 A1* | 7/2003 | Levy ............... A61B 17/7266 606/63 |
| 2004/0002759 A1 | 1/2004 | Ferree |
| 2004/0093081 A1 | 5/2004 | Nilsson et al. |
| 2004/0102853 A1 | 5/2004 | Boumann et al. |
| 2004/0138756 A1 | 7/2004 | Reeder |
| 2004/0220678 A1 | 11/2004 | Chow et al. |
| 2004/0230193 A1* | 11/2004 | Cheung ............... A61B 17/7266 606/63 |
| 2005/0119757 A1 | 6/2005 | Hassler et al. |
| 2005/0124990 A1* | 6/2005 | Teague ............... A61B 17/1735 606/53 |
| 2005/0251265 A1 | 11/2005 | Calandruccio et al. |
| 2005/0261768 A1* | 11/2005 | Trieu ............... A61B 17/7065 623/17.11 |
| 2005/0283159 A1* | 12/2005 | Amara ............... A61B 17/7266 606/75 |
| 2006/0015181 A1* | 1/2006 | Elberg ............... A61B 17/7062 623/16.11 |
| 2006/0052725 A1 | 3/2006 | Santilli |
| 2006/0052878 A1 | 3/2006 | Schmieding |
| 2006/0074492 A1 | 4/2006 | Frey |
| 2006/0084998 A1 | 4/2006 | Levy et al. |
| 2006/0085075 A1 | 4/2006 | McLeer |
| 2006/0247787 A1 | 11/2006 | Rydell et al. |
| 2007/0038303 A1 | 2/2007 | Myerson et al. |
| 2007/0123993 A1 | 5/2007 | Hassler et al. |
| 2007/0142920 A1 | 6/2007 | Niemi |
| 2007/0156241 A1 | 7/2007 | Reiley et al. |
| 2007/0185584 A1 | 8/2007 | Kaufmann et al. |
| 2007/0198088 A1* | 8/2007 | Biedermann ............... A61B 17/6491 623/17.11 |
| 2007/0213831 A1 | 9/2007 | de Cubber |
| 2007/0239158 A1 | 10/2007 | Trieu et al. |
| 2008/0039949 A1 | 2/2008 | Meesenburg et al. |
| 2008/0132894 A1 | 6/2008 | Coilard-Lavirotte et al. |
| 2008/0154385 A1 | 6/2008 | Trail et al. |
| 2008/0177262 A1* | 7/2008 | Augoyard ............... A61B 17/68 606/70 |
| 2008/0195219 A1 | 8/2008 | Wiley et al. |
| 2008/0221697 A1 | 9/2008 | Graser |
| 2008/0221698 A1 | 9/2008 | Berger |
| 2008/0234763 A1 | 9/2008 | Patterson et al. |
| 2008/0269908 A1 | 10/2008 | Warburton |
| 2009/0005821 A1 | 1/2009 | Chirico et al. |
| 2009/0012564 A1* | 1/2009 | Chirico ............... A61B 17/1671 606/246 |
| 2009/0138096 A1 | 5/2009 | Myerson et al. |
| 2009/0254189 A1 | 10/2009 | Scheker |
| 2009/0254190 A1 | 10/2009 | Gannoe et al. |
| 2010/0010637 A1 | 1/2010 | Pequignot |
| 2010/0016905 A1 | 1/2010 | Greenhalgh et al. |
| 2010/0016982 A1 | 1/2010 | Solomons |
| 2010/0057214 A1 | 3/2010 | Graham et al. |
| 2010/0121390 A1 | 5/2010 | Kleinman |
| 2010/0131014 A1* | 5/2010 | Peyrot ............... A61B 17/7266 606/300 |
| 2010/0131072 A1 | 5/2010 | Schulte |
| 2010/0161068 A1 | 6/2010 | Lindner et al. |
| 2010/0185295 A1 | 7/2010 | Emmanuel |
| 2010/0228301 A1 | 9/2010 | Greenhalgh et al. |
| 2010/0249942 A1 | 9/2010 | Goswami et al. |
| 2010/0256770 A1 | 10/2010 | Hakansson et al. |
| 2010/0262254 A1 | 10/2010 | Lawrence et al. |
| 2011/0004317 A1 | 1/2011 | Hacking et al. |
| 2011/0093084 A1 | 4/2011 | Morton |
| 2011/0093085 A1 | 4/2011 | Morton |
| 2011/0144644 A1 | 6/2011 | Prandi et al. |
| 2011/0301652 A1 | 12/2011 | Reed et al. |
| 2011/0301653 A1* | 12/2011 | Reed ............... A61B 17/1604 606/319 |
| 2012/0029579 A1 | 2/2012 | Bottlang et al. |
| 2012/0065692 A1 | 3/2012 | Champagne et al. |
| 2012/0083791 A1* | 4/2012 | Cheney ............... A61B 17/8872 606/99 |

(56) References Cited

U.S. PATENT DOCUMENTS

| | | | |
|---|---|---|---|
| 2012/0089197 A1* | 4/2012 | Anderson | A61B 17/7233 606/310 |
| 2013/0053975 A1 | 2/2013 | Reed et al. | |
| 2013/0060295 A1 | 3/2013 | Reed et al. | |
| 2013/0066435 A1 | 3/2013 | Averous et al. | |
| 2013/0131822 A1 | 5/2013 | Lewis et al. | |
| 2013/0150965 A1 | 6/2013 | Taylor et al. | |
| 2013/0190761 A1* | 7/2013 | Prandi | A61B 17/68 606/62 |
| 2014/0058462 A1 | 2/2014 | Reed et al. | |
| 2014/0142715 A1 | 5/2014 | McCormick | |
| 2014/0180428 A1 | 6/2014 | McCormick | |
| 2014/0188239 A1 | 7/2014 | Cummings | |
| 2015/0073413 A1* | 3/2015 | Palmer | A61B 17/7266 606/63 |
| 2015/0223849 A1* | 8/2015 | McCormick | A61B 17/7291 606/63 |
| 2017/0065310 A1* | 3/2017 | Girod | A61B 17/68 |

FOREIGN PATENT DOCUMENTS

| | | |
|---|---|---|
| CA | 2836654 A1 | 6/2014 |
| CA | 2837497 A1 | 6/2014 |
| EP | 0042808 A1 | 12/1981 |
| EP | 0420794 A1 | 4/1991 |
| EP | 0454645 A1 | 10/1991 |
| EP | 1300122 A2 | 4/2003 |
| EP | 1356794 A3 | 11/2003 |
| EP | 1582159 A1 | 10/2005 |
| EP | 1923012 A1 | 5/2008 |
| FR | 2663838 A1 | 1/1992 |
| FR | 2725126 A1 | 4/1996 |
| FR | 2783702 A1 | 3/2000 |
| FR | 2787313 A1 | 6/2000 |
| FR | 2794019 A1 | 12/2000 |
| FR | 2801189 A1 | 5/2001 |
| FR | 2846545 A1 | 5/2004 |
| FR | 2884406 | 10/2006 |
| GB | 2119655 A | 11/1983 |
| GB | 2430625 B | 4/2007 |
| JP | 60145133 A | 7/1985 |
| JP | 03-001854 A | 8/1991 |
| JP | 7303662 A | 11/1995 |
| JP | 2004535249 A | 11/2004 |
| JP | 3648687 B2 | 5/2005 |
| JP | 2007530194 A | 11/2007 |
| JP | 2008188411 A | 8/2008 |
| JP | 2008537696 A | 9/2008 |
| JP | 4695511 B2 | 6/2011 |
| JP | 5631597 B2 | 11/2014 |
| KR | 20070004513 A | 1/2007 |
| KR | 20070022256 A | 2/2007 |
| KR | 101004561 B1 | 1/2011 |
| KR | 101235983 B1 | 2/2013 |
| WO | 9116014 A1 | 10/1991 |
| WO | 9625129 A1 | 8/1996 |
| WO | 9641596 A1 | 12/1996 |
| WO | 9726846 A1 | 7/1997 |
| WO | 9733537 A1 | 9/1997 |
| WO | 0117445 A1 | 3/2001 |
| WO | 03084416 A1 | 10/2003 |
| WO | 2005020830 A1 | 3/2005 |
| WO | 2005063149 A1 | 7/2005 |
| WO | 2005104961 A1 | 11/2005 |
| WO | 2006109004 A1 | 10/2006 |
| WO | 2008057404 A2 | 5/2008 |
| WO | 2008112308 A1 | 9/2008 |
| WO | 2009103085 A1 | 8/2009 |
| WO | 2011130229 A1 | 10/2011 |

OTHER PUBLICATIONS

International Search Report for PCT/FR2008/050453 dated Nov. 4, 2008.

* cited by examiner

METHOD OF OSTEOSYNTHESES OR ARTHRODESIS OF TWO-BONE PARTS, IN PARTICULAR OF THE HAND AND / OR FOOT

CROSS-REFERENCE TO RELATED APPLICATIONS

This application is a continuation of U.S. application Ser. No. 13/896,894, filed May 17, 2013, which is a continuation of U.S. application Ser. No. 11/911,405, filed Mar. 17, 2008, which is a US national phase of PCT Publication PCT/FR2006/050345, filed 12 Apr. 2006, published 19 Oct. 2006 as WO2006/109004, and claiming the priority of French Application No. 0550957, filed Apr. 14, 2005, whose entire disclosures are herewith incorporated by reference.

FIELD OF THE INVENTION

The invention relates to the technical field of orthopaedic implants, particularly for arthrodesis and osteosyntheses.

It may be recalled that the object of an arthrodesis is to obtain very good stability both primary and secondary, and to place, or to maintain, in compression, two bone parts or bone fragments that should be consolidated. Stability is a critical factor for obtaining consolidation, while minimizing the attendant problems such as pain, swelling, etc. The compressive action serves to consolidate the osteotomy more rapidly in the position selected by the surgeon during the operation.

Various technical solutions have been proposed for carrying out an arthrodesis, particularly in the foot, the hand, the wrist, etc. Mention can be made, for example, of basic staples without shape memory which do not produce a compression, as opposed to memory staples which serve to place the two bone parts to be consolidated in compression, which corresponds to the objective.

However, to obtain satisfactory stability, it is necessary to place two, or even three staples, in different planes. This increases the dimensions considerably, thereby limiting applications (metacarpo-phalangeal joint, for example).

Extramedullary plates and screws have also been proposed, requiring an alternatively large dimension. In this respect, their miniaturization is difficult to conceive, because this could raise problems of strength and stiffness. Some types of screws can be used in intramedullary osteosynthesis, but they raise positioning difficulties (passage through the pad in particular).

Use can also be made of pins which have a smaller size. However, the stability obtained is unsatisfactory and it is necessary to withdraw them.

Intramedullary nails are also known, but they require supplementary stapling in order to prevent the bone parts to be joined from rotating relative to each other.

OBJECT OF THE INVENTION

It is the object of the invention to remedy these drawbacks simply, safely, effectively and efficiently.

The problem that the invention proposes to solve is to permit the fixation of two bone parts to one another, rigidly with dynamic and retentive compression, in order to obtain a reliable and rapid osteosynthesis.

SUMMARY OF THE INVENTION

To solve such a problem, an intramedullary arthrodesis element has been designed and developed which consists of a body with an elongated shape having, in succession, from one of its ends, a fixation zone cooperating with one of the bone parts to be immobilized, a median zone suitable for withstanding shear and bending stresses, and a fixation zone in the other bone part to be immobilized, each of the fixation zones being profiled and made from a material suitable for enabling introduction into the bone parts without a finger- or toe-tip approach, followed by a fixation in the bone parts, while avoiding any rotational movement, withstanding the tensile stresses, and maintaining a compressive force.

The invention has a particularly advantageous application, which can however not be considered as limiting, for the preparation of arthrodesis in the proximal and median phalanges, for proximal interphalangeal joints and distal interphalangeal joints, in the hand or foot.

To solve the problem of taking account of the anatomy, and particularly of the internal shrinkage of the bone, the median zone is linked to at least one of the fixation zones by a connecting zone.

To solve the problem of permitting implantation of the element followed by compression of the bone fragments, the fixation zones are made from a shape-memory material to be deformed by thermal and/or mechanical action.

To produce the fixation zones, which may be identical or not, various technical solutions are feasible, according in particular to the type of arthrodesis performed and the joints to be treated.

For example:

one of the fixation zones has two tabs or wings separable under the action of the shape memory;

one of the fixation zones has a tab or rod which can be curved under the action of the shape memory;

one of the fixation zones has, in its thickness, a slot for permitting deformation by elasticity, or memory, under the action of the shape memory.

In one embodiment, the overall body has a flat cross-section.

BRIEF DESCRIPTION OF THE DRAWING

The invention is described below in greater detail in conjunction with the figures of the drawings appended hereto in which.

SPECIFIC DESCRIPTION

Figure 1:
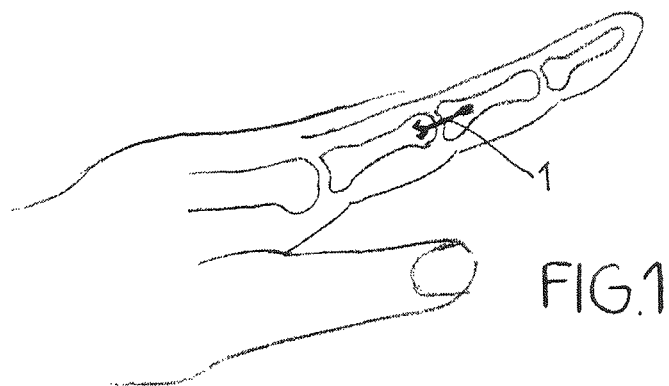
FIG. 1 is a schematic plan view showing the placement of the intramedullary arthrodesis element of the invention between a proximal phalange and a median phalange to consolidate the proximal interphalangeal joint.

The arthrodesis element of the invention consists of an elongated body 1. Each of the ends of the body 1 is conformed to produce a fixation zone 1a linked to a fixation zone 1b.

Between the two fixation zones 1a and 1b, at least one median zone 1c is formed capable of withstanding shear and bending stresses. In general, the shear and bending stresses are applied to the bone site to be consolidated. The shape of this median zone 1c is adapted to the internal shape of the bone. Its length is determined in order to allow a slight offset in the centering.

For information, and in a non-limiting manner, this median zone may have a rectangular cross-section measuring about 2 to 3 mm*1 to 1.5 mm and a length of about 3 to 5 mm for the foot and the hand.

The fixation zones 1a and 1b are conformed to prevent any rotational movement, resist tension, and maintain manual compression applied at the time of the implant by the surgeon in order to reduce the site. To obtain this result, the fixation zones 1a and 1b are made from a shape-memory material to be deformed by thermal action (tepid memory) or mechanical action (superelasticity) (see U.S. Pat. No. 5,958, 159). The goal, in the fixation zones, considering their profile on the one hand and the type of material on the other, is to permit an introduction into the bone parts, particularly dorsally without a finger- or toe-tip approach, on the one hand, and to produce a fixation in the bone portion in order to obtain or to maintain the desired compressive force, on the other. The fixation zones 1a and 1b are identical or not, according to the type of bone and its morphology.

Depending on the type of arthrodesis performed, that is, the type of interphalangeal joint to be consolidated for example, the fixation zones 1a and 1b may have different embodiments.

For example, one of the fixation zones 1a has two tabs or wings that are separable under a thermal action for example. Otherwise, these fixation zones 1a may have a single tab or rod which can be curved under the action of a memory of the component material. Otherwise, the fixation zone 1b has, in its thickness, a slot to permit deformation by elasticity, under thermal action for example, and to maintain the position by pressing on the length of the bone.

According to another feature of the invention, to take account of the anatomy of the various phalanges for example, that is the internal shrinkage of the bone (hourglass shape), the median zone 1c is linked to at least one of the fixation zones 1b by a thinner connecting zone 1d.

Reference can be made to the figures of the drawings which show an embodiment of an intramedullar arthrodesis element.

In this embodiment, the body 1 has, at one of its ends, a fixation zone 1a in the form of two tabs or wings 1a1 1a2. This fixation zone 1a is prolonged by a median zone 1c of generally substantially triangular shape in a plan view. The median zone 1c is connected to the other end fixation zone 1b by a connecting zone 1d having a generally rectangular shape in a plan view. The fixation zone 1b has, in its thickness, a slot of generally oblong shape 1b1.

Figures 2, 3:
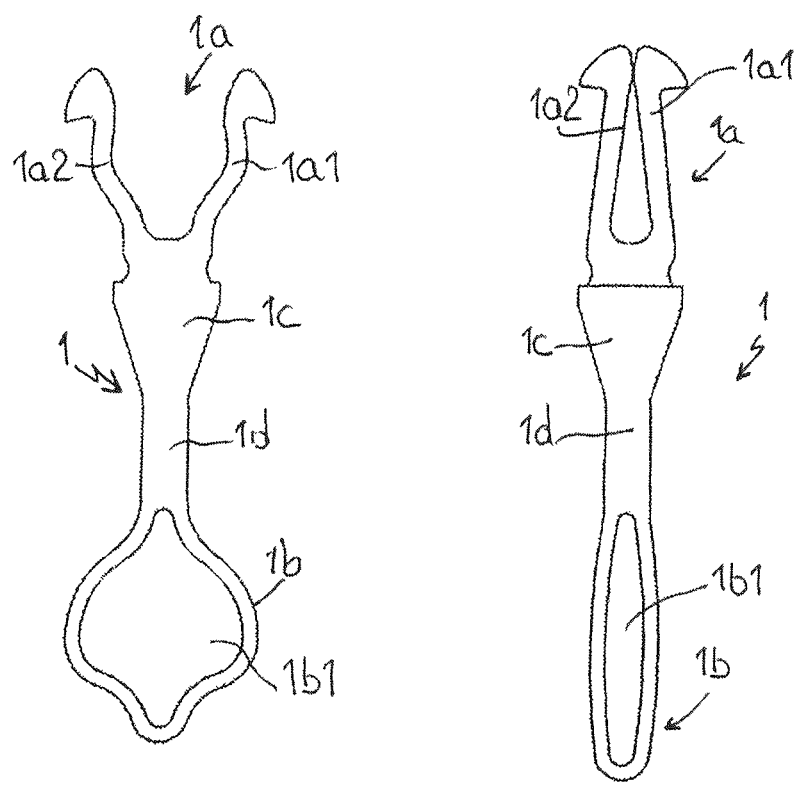
FIG. 2 is a plan view of an embodiment of the arthrodesis element at the time of its introduction.
FIG. 3 is a view corresponding to FIG. 2 showing the arthrodesis element after its implant to produce the compression.
Figure 4:
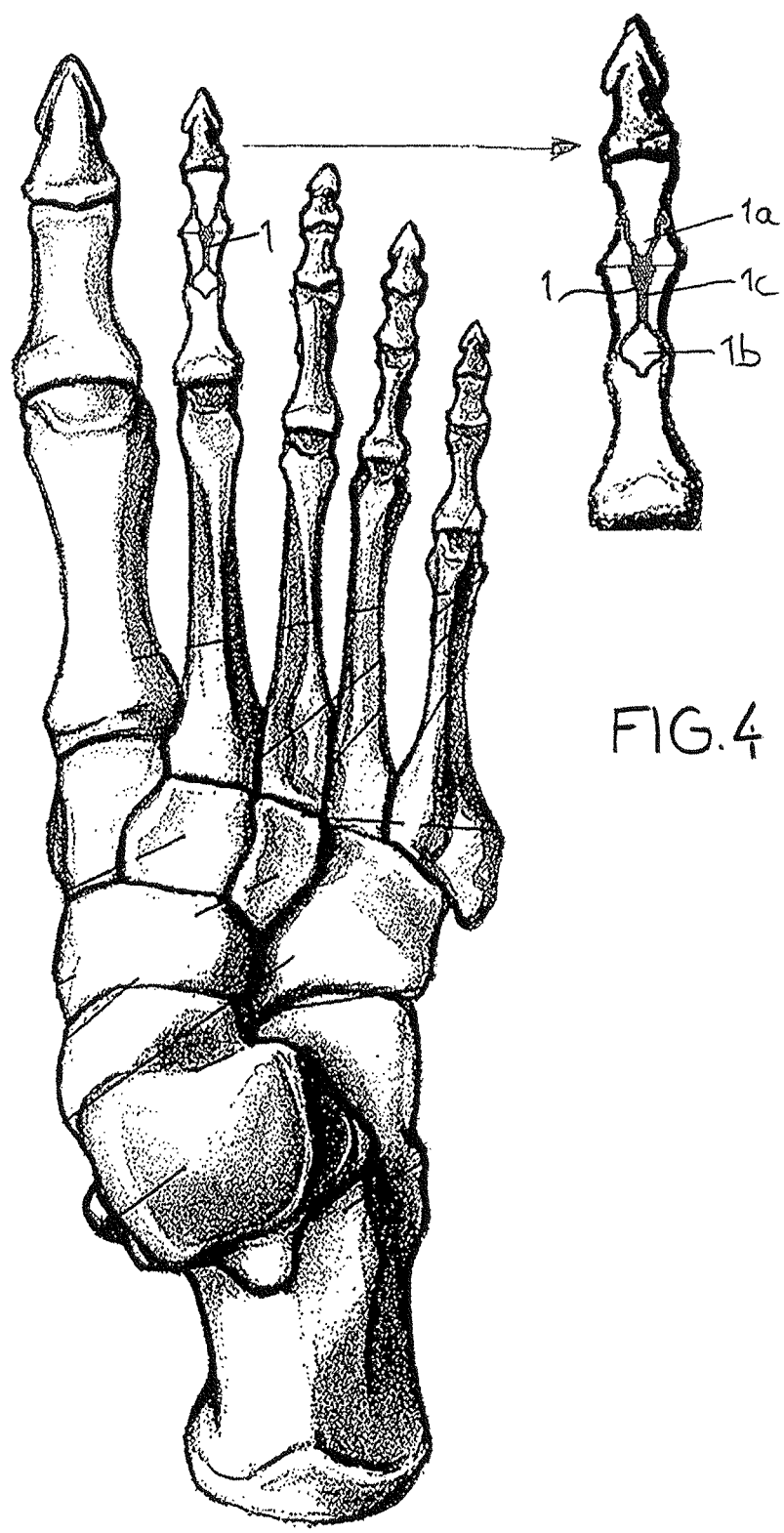
FIG. 4 shows the placement of the element of the invention in a toe.

Reference can be made to FIG. 2 which shows the element at the time of its introduction, that is before separation of the tabs 1a1 and 1a2, and the opening of the slot 1b1. For example, this configuration is obtained when the overall element is subject to a temperature much lower than that of the human body for example. Conversely, after implantation (FIG. 3), under the effect of body heat, the tabs 1a1 and 1a2 separate, in the same way as the slot 1b1, concomitantly causing a deformation of the fixation zone 1b.

It should be noted that the profile of the median zone 1c prevents penetration when the site is reclosed.

In an alternative embodiment, the connecting zone 1d can be split to benefit from a swelling effect by shape memory and strengthening of the anchoring in the diaphyseal zone.

It should be recalled that the inventive element is ideal for the treatment of the hammer- or claw-toe syndrome, by performing an arthrodesis in the phalanges P1 and P2 on the radii 2 to 5, while observing that such applications must not be considered as limiting, by means of essentially dimensional adjustments (finger reimplants, arthrodesis of the distal interphalangeal joint and of the proximal interphalangeal joint of the hand, and the arthrodesis of the big toe).

Obviously, the entire arthrodesis element of the invention may have constructive features suitable for improving the fixation and compression in particular.

For example:
notches on the tabs on one of the sides for better fixation in the ethmoid bone;
wavy tabs implanted (straight before implant)
to permit shortening and hence an additional compression of the arthrodesis site compared with a simple fixation;
a tapered central zone to avoid undesirable
penetration of the implant at the time when the site is to be closed.

For information, the memory used is preferably a tepid memory, so that heating is unnecessary because of the lack of access. The opening begins at above 15 to 20° C. and stops at about 30 to 35° C.

The operating technique remains conventional.

The invention claimed is:

1. A fixation device comprising:
a median zone having a substantially triangular shape;
a first fixation zone including first and second tabs that, in a separated configuration, extend away from each other from an end of the median zone, the first fixation zone having a first region adjacent the median zone and a second region adjacent the first region;
wherein, within the first region of the first fixation zone, an inner surface of each of the first and second tabs of the first fixation zone extends outwardly and proximally from the median zone to a first point on each of the first and second tabs to form an arch extending continuously from the first point on the first tab to the first point on the second tab, and from each of the first points, the inner surface of each of the first and second tabs extends toward a second point, and
within the second region of the first fixation zone, the inner surface of each of the first and second tabs of the first fixation zone extends outwardly from each second point to a respective third point so that the inner surface of each of the first and second tabs from the second point to the third point is arcuate and convex.

2. The device of claim 1, wherein each tab in a first fixation zone includes at least one outwardly projecting barb adapted to engage bone, the barb including a decline toward the distal end of the fixation device.

3. The device of claim 1, further comprising a generally rectangular connecting zone adjacent the median zone.

4. The device of claim 1, further comprising a second fixation zone including first and second tabs extending outwardly in a proximal direction away from a distal tip.

5. The device of claim 4, wherein the second fixation zone is positioned at one end of the median zone and the first fixation zone is positioned at an opposite end of the median zone, wherein both the first and second tabs of the second fixation zone and the first and second tabs of the first fixation zone extend proximally.

6. The device of claim 1, wherein the first and second tabs of the first fixation zone comprise a first width in the separated position.

7. The device of claim 6, wherein the first and second tabs of the first fixation zone comprise a second width in an implantable position that is narrower than this first width.

8. The device of claim 4, wherein the first and second tabs of the second fixation zone have a first width in an open position.

9. The device of claim 8, wherein the first and second tabs of the second fixation zone have a second width in an implantable position that is narrower than the first width.

10. A fixation device comprising:
a body extending between a proximal end and a distal end including a proximal fixation zone, a distal fixation zone and a median zone positioned between the proximal and distal fixation zones, the proximal fixation zone including a first tab and a second tab that, in a separated zone, extend from a proximal end of the median zone in a radially outward direction to a first tab end and a second tab end,
wherein an inner surface of the first and second tabs forms a first length extending from adjacent the median zone to a first point on each of the first and second tabs with an increasing slope along the first length, forms a second length along each of the first and second tabs with a decreasing slope from the first point to a second point, and forms a third length along each of the first and second tabs with an increasing slope from the second point to the respective first tab end and second tab end.

11. The device of claim 10, wherein the decreasing slope from the first point to the second point defines a concave surface.

12. The device of claim 10, wherein the increasing slope from the second point to the first and second tab ends defines a convex surface.

13. The device of claim 10, wherein the first tab end and second tab end each form an apex of each of the first and second tabs and, from the apex, the inner surface of each tab extends to a barb positioned on an outer surface of each of the first and second tabs.

14. The device of claim 10, wherein the distal fixation zone includes a first tab and a second tab extending in a radially outward direction from a distal-most end towards the median zone.

15. The device of claim 14, wherein the first and second tabs of the proximal fixation zone and the first and second tabs of the distal fixation zone both extend radially outwards in a proximal direction.

16. The device of claim 15, further comprising a generally rectangular connecting zone positioned between the median zone and the distal fixation zone.

17. A fixation device comprising:
a monolithic body extending between a proximal end and a distal end including a proximal fixation zone, a distal fixation zone and a median zone positioned between the proximal and distal fixation zones, the proximal fixation zone including a first tab and a second tab, the first and second tabs each having a first region adjacent a second region, and the distal fixation zone including a first tab and a second tab extending in a radially outward direction from a distal-most end towards the median zone,
wherein the proximal fixation zone has an open position, in the open position an inner surface of the first region of the first and second tabs forms a convex surface and an inner surface of the second region of the first and second tabs forms a concave surface.

18. The fixation device of claim 17, wherein the proximal fixation zone has an implantable position, in the implantable position the inner surface of the second region of the first and second tabs is substantially linear.

19. The fixation device of claim 17, wherein the convex surface is proximal to the concave surface.

20. The fixation device of claim 17, wherein the inner surface of the first region of the first and second tabs forms an arch.

* * * * *